(12) United States Patent
Chiku et al.

(10) Patent No.: US 11,255,849 B2
(45) Date of Patent: *Feb. 22, 2022

(54) KIT FOR QUANTITATIVELY DETERMINING SUBSTANCE TO BE MEASURED IN BIOLOGICAL SAMPLE

(71) Applicant: FUJIFILM Corporation, Tokyo (JP)

(72) Inventors: Hiroyuki Chiku, Kanagawa (JP); Noriyuki Kasagi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 746 days.

This patent is subject to a terminal disclaimer.

(21) Appl. No.: 16/115,595

(22) Filed: Aug. 29, 2018

(65) Prior Publication Data

US 2018/0372731 A1 Dec. 27, 2018

Related U.S. Application Data

(63) Continuation of application No. PCT/JP2017/007745, filed on Feb. 28, 2017.

(30) Foreign Application Priority Data

Feb. 29, 2016 (JP) .............................. JP2016-037299
Dec. 6, 2016 (JP) .............................. JP2016-236621

(51) Int. Cl.
*G01N 33/543* (2006.01)
*G01N 33/53* (2006.01)
(Continued)

(52) U.S. Cl.
CPC ....... *G01N 33/54306* (2013.01); *G01N 21/64* (2013.01); *G01N 21/648* (2013.01);
(Continued)

(58) Field of Classification Search
None
See application file for complete search history.

(56) References Cited

U.S. PATENT DOCUMENTS 5,631,138 A 5/1997 Kano et al.
2009/0203151 A1 8/2009 Matsuno et al.
(Continued)

FOREIGN PATENT DOCUMENTS

CN 1309771 8/2001
CN 103033492 4/2013
(Continued)

OTHER PUBLICATIONS

"Search Report of Europe Counterpart Application," dated Feb. 26, 2019,p. 1-p. 8.
(Continued)

*Primary Examiner* — Rebecca M Giere
(74) *Attorney, Agent, or Firm* — JCIPRNET (57) ABSTRACT

An object of the present invention is to provide a kit in which a quantitative determination of a substance to be measured in a biological sample can be carried out with high accuracy, even in a case where the substance to be measured includes a plurality of substances having different structures. According to the present invention, a kit for quantitatively determining a substance to be measured in a biological sample, the kit including fluorescent particles that have a first binding substance capable of binding to the substance to be measured; and a substrate that has a detection region having a second binding substance capable of binding to any one of the substance to be measured and the first binding substance, in which the substance to be measured includes at least three types of substances having different structures, and the first binding substance includes at least three types of binding substances which are capable of binding to the at least three (Continued)

types of substances having different structures, respectively, is provided.

5 Claims, 2 Drawing Sheets

(51) Int. Cl.
*G01N 21/64* (2006.01)
*G01N 21/78* (2006.01)

(52) U.S. Cl.
CPC ......... *G01N 21/6428* (2013.01); *G01N 21/78* (2013.01); *G01N 33/53* (2013.01); *G01N 33/543* (2013.01); *G01N 2021/6439* (2013.01)

(56) References Cited

U.S. PATENT DOCUMENTS

2013/0078738 A1  3/2013  Watanabe et al.
2014/0295468 A1* 10/2014  Kasagi ............. G01N 33/54366
                                                    435/7.93

FOREIGN PATENT DOCUMENTS

| EP | 1143251 | 10/2001 |
|----|---------|---------|
| JP | S54149700 | 11/1979 |
| JP | H0135372 | 2/1989 |
| JP | H03216553 | 9/1991 |
| JP | H08145995 | 6/1996 |
| JP | 2009080019 | 4/2009 |
| JP | 2009192222 | 8/2009 |
| JP | 2014119418 | 6/2014 |
| WO | 2012055069 | 5/2012 |

OTHER PUBLICATIONS

"Office Action of China Counterpart Application", dated Jun. 30, 2020, with English translation thereof, pp. 1-14.
Xie Huan-Long et al., "Simultaneous Detection of Malachite Green and Leucomalachite Green Based on Hybrid Antibody ELISA Analysis Method", Modern Food Science and Technology, Mar. 2015, submit with English abstract, pp. 1-6.
Office Action of China Counterpart Application, with English translation thereof, dated Mar. 12, 2021, pp. 1-14.
"International Search Report (Form PCT/ISA/210) of PCT/JP2017/007745," dated Jun. 6, 2017, with English translation thereof, pp. 1-5.
"Written Opinion of the International Searching Authority (Form PCT/ISA/237) of PCT/JP2017/007745," dated Jun. 6, 2017, with English translation thereof, pp. 1-9.
Seibert RL et al., "Evaluation of a semiquantitative SNAP test of measurement of bile acids in dogs," PeerJ., Aug. 26, 2014, pp. 1-11.
"Office Action of China Counterpart Application" with English translation thereof, dated Jun. 18, 2021, p. 1-p. 17.

* cited by examiner

KIT FOR QUANTITATIVELY DETERMINING SUBSTANCE TO BE MEASURED IN BIOLOGICAL SAMPLE

CROSS-REFERENCE TO RELATED APPLICATIONS

This application is a Continuation of PCT International Application No. PCT/JP2017/007745 filed on Feb. 28, 2017, which claims priority under 35 U.S.C § 119(a) to Japanese Patent Application No. 2016-037299 filed on Feb. 29, 2016 and Japanese Patent Application No. 2016-236621 filed on Dec. 6, 2016. Each of the above application(s) is hereby expressly incorporated by reference, in its entirety, into the present application.

BACKGROUND OF THE INVENTION

1. Field of the Invention

The present invention relates to a kit for quantitatively determining a substance to be measured in a biological sample.

2. Description of the Related Art

A fluorescence detection method has been in wide use as a highly sensitive and simple measurement method for quantitatively determining a substance to be measured such as proteins, enzymes, and inorganic compounds which are contained in a biological sample. The fluorescence detection method is a method in which fluorescence emitted in a case where a sample considered to include a substance to be measured which is excited by light of a specific wavelength so as to emit fluorescence, is irradiated with excitation light of the specific wavelength, is detected, and thus the presence of the substance to be measured is confirmed. In a case where the substance to be measured is not a fluorescent substance, a substance that specifically binds to the substance to be measured is labeled with a fluorescent dye and brought into contact with a sample, and thereafter, in the same manner as above, fluorescence emitted in a case where the sample is irradiated with the excitation light is detected, and thus the presence of the substance to be measured can be confirmed.

In the fluorescence detection method as described above, in order to improve detection sensitivity, a method utilizing the effect of electric field enhancement by plasmon resonance has been known. In this method, in order to generate plasmon resonance, a sensor chip including a metal film provided in a predetermined region on a transparent support is prepared. The excitation light is allowed to enter an interface between the support and the metal film from a side opposite to the metal film formation surface of the support at an angle equal to or greater than a total reflection angle. Surface plasmons are generated in the metal film by irradiation with the excitation light, fluorescence is enhanced by the electric field enhancement effect due to generation of the surface plasmons, and therefore a signal/noise ratio (S/N ratio) is improved. In the fluorescence detection method by surface plasmon excitation (Surface Plasmon Fluorescence, hereinafter, will be referred to as "SPF method"), a signal enhancement of about 10 times as compared with a fluorescence detection method by epi-excitation (hereinafter, will be referred to as "epifluorescence method") is obtained, and thus high sensitive measurement is possible.

A bile acid is a generic term for compounds which has a cholanic acid skeleton and is a steroid derivative present in the bile of mammals, and representative examples thereof include a cholic acid, a deoxycholic acid, and a chenodeoxycholic acid. As a method for measuring bile acids, for example, JP1989-35372A (JP-H01-35372A) discloses a method for determining the presence or absence or an amount of an analyte in a sample, the method including (a) mixing the sample with a non-metallic labeling composition composed of colloidal non-metallic particles to which a binding component capable of specifically recognizing the analyte is bound, and then (b) determining the presence or absence or an amount of an analyte/colloidal non-metallic particles complex. JP1989-35372A (JP-H01-35372A) disclosed that the binding component bound to the non-metallic particles is selected from the group consisting of an antigen, a hapten, and an antibody, and as analytes, a cholic acid, a deoxycholic acid, a chenodeoxycholic acid, and the like are exemplified.

SUMMARY OF THE INVENTION

As described above, a fluorescence detection method by surface plasmon excitation has been known as a simple measurement method by which high sensitive measurement is possible, but in a case where a substance to be measured includes a plurality of substances having different structures, the measurement accuracy was not sufficiently satisfied. In particular, in order to quantitatively determining three or more types of substances having different structures such as bile acids, it is desired to provide a simple measurement method with high reproducibility.

An object of the present invention is to provide a kit in which a quantitative determination of the substance to be measured in a biological sample can be carried out with high accuracy, even in a case where the substance to be measured includes a plurality of substances having different structures.

The inventors of the present invention conducted intensive studies to solve the above-described problems, and as a result, have found that the problems can be solved by using at least three types of binding substances as first binding substances in a kit for quantitatively determining the substance to be measured in a biological sample, the kit including fluorescent particles that have a first binding substance capable of binding to the substance to be measured; and a substrate that has a detection region having a second binding substance capable of binding to any one of the substance to be measured and the first binding substance. The present invention has been completed based on these findings. That is, according to the present invention, the following invention is provided.

(1) A kit for quantitatively determining a substance to be measured in a biological sample, the kit comprising: fluorescent particles that have a first binding substance capable of binding to the substance to be measured; and a substrate that has a detection region having a second binding substance capable of binding to any one of the substance to be measured and the first binding substance, in which the substance to be measured includes at least three types of substances having different structures, and the first binding substance includes at least three types of binding substances which are capable of binding to the at least three types of substances having different structures, respectively.

(2) The kit according to (1), in which each fluorescent particle of the fluorescent particles has the at least three types of binding substances.

(3) The kit according to (1) or (2), in which the second binding substance is the at least three types of substances having different structures or a conjugate of the three types of substances having different structures and a carrier.

(4) The kit according to any one of (1) to (3), in which the first binding substance includes a cholic acid antibody, a deoxycholic acid antibody, and a chenodeoxycholic acid antibody.

(5) The kit according to any one of (1) to (4), in which the second binding substance includes a cholic acid and/or a cholic acid-albumin conjugate, a deoxycholic acid and/or a deoxycholic acid-albumin conjugate, and a chenodeoxycholic acid and/or a chenodeoxycholic acid-albumin conjugate.

(6) The kit according to any one of (1) to (5), in which the fluorescent particles are fluorescent latex particles.

(7) The kit according to any one of (1) to (6), in which the detection region is a gold film surface.

According to the kit of the present invention, the quantitative determination of the substance to be measured in the biological sample can be carried out with high accuracy, even in a case where the substance to be measured includes a plurality of substances having different structures.

DESCRIPTION OF THE PREFERRED EMBODIMENTS

Hereinafter, the present invention will be described in detail.

[Kit for Quantitatively Determining Substance to be Measured in Biological Sample]

A kit for quantitatively determining a substance to be measured in a biological sample according to the present invention, is a kit including fluorescent particles that have a first binding substance capable of binding to the substance to be measured; and a substrate that has a detection region having a second binding substance capable of binding to any one of the substance to be measured and the first binding substance, in which the substance to be measured includes at least three types of substances having different structures, and the first binding substance includes at least three types of binding substances which are capable of binding to the at least three types of substances having different structures, respectively.

In the present invention, even in a case where the substance to be measured includes the at least three types of substances having different structures, the quantitative determination of the substance to be measured in the biological sample can be carried out with high accuracy by using, as the first binding substances, at least the three types of binding substances which are capable of binding to at least the three types of substances having different structures, respectively. In the present invention, a problem of improving the measurement accuracy in a case of quantitatively determining the three types of substances having different structures such as bile acids has been newly found, and the above-described problem is solved by using the at least three types of binding substances as the first binding substances.

(Biological Sample)

The biological sample is not particularly limited as long as the biological sample is a sample which may contain the substance to be measured, and examples thereof include a biological sample, particularly body fluids (for example, blood, blood serum, blood plasma, cerebrospinal fluid, tear fluid, sweat, urine, pus, nasal discharge, or expectoration) of animals (for example, humans, dogs, cats, and the like), excretas (for example, feces), organs, tissues, membrana mucosa, skin, and the like.

(Substance to be Measured)

The substance to be measured is not particularly limited as long as the substance to be measured includes the at least three types of substances having different structures, and examples thereof include bile acids, cholesterols, proteins, and the like.

The main role of the bile acids is to promote the formation of micelles in the digestive tract so that dietary fat becomes likely to be absorbed. A bile acid which is biosynthesized in the liver is called a primary bile acid. In addition, some bile acids undergo microbial conversion in the intestinal tract, and a metabolite thereof is called a secondary bile acid. The bile acid is generally associated with glycine and taurine, and such a bile acid is called a conjugated bile acid (a bile salt).

A rapid and simple method for measuring a concentration of serum bile acids in dogs and cats has been recognized as a high sensitive and specific examination reflecting hepatocyte functions and enterohepatic circulation. In studies on serum bile acids, in dogs and cats which exhibit a high level of liver enzyme activity but are not accompanied with jaundice and in which clinical signs are unclear and cannot be interpreted, the usefulness of the serum bile acids has been demonstrated in order to detect hepatobiliary diseases that require clinically definite diagnosis. In addition, a quantitative determination of fasting and postprandial bile acids has been recommended in order to increase a diagnostic rate in diagnosis of congenital portosystemic shunt. In a case where a concentration of bile acids shows a high value, acute hepatitis, chronic liver disease, cholestasis, intestinal bacterial proliferation, portosystemic shunt (PSS), and the like are suspected. In a case where a concentration of bile acids shows a low value, intestinal malabsorption is suspected.

Such bile acids are present as aggregates of compounds having slightly different structures, and specifically, ten types of compounds are present. In the case of dogs and cats, three types of taurine conjugates of a cholic acid, a deoxycholic acid, and a chenodeoxycholic acid account for almost 100% as bile acids. For example, a percentage of the three types of bile acids having different structures in blood of dogs is cholic acid-taurine conjugate: deoxycholic acid-taurine conjugate: chenodeoxycholic acid-taurine conjugate=74%:20%:6%, in terms of average value (Journal of the Japanese Society of Veterinary Science, 52 (2), 1990). The structures of the cholic acid, the deoxycholic acid, and the chenodeoxycholic acid are as follows.

Cholic acid

Deoxycholic acid

Chenodeoxycholic acid (First Binding Substance)

The first binding substance used in the present invention is a substance capable of binding to the substance to be measured. As the first binding substance, an antigen, an antibody, or a complex thereof can be used, but the first binding substance is not limited thereto. The first binding substances are preferable antibodies. In a case where the first binding substances are the antibodies, as the antibodies capable of binding to the substance to be measured, for example, an antiserum prepared from blood serum of an animal immunized with the substance to be measured, an immunoglobulin fraction purified from an antiserum, a monoclonal antibody obtained by cell fusion using spleen cells of an animal immunized with the substance to be measured, fragments thereof [for example, $F(ab')_2$, Fab, Fab', or Fv], and the like can be used. The preparation of these antibodies can be carried out by using a general method. Furthermore, an antibody modified as a case of a chimeric antibody or the like may be used, or a commercially available antibody also may be used as long as the antibody is an antibody prepared from blood serum of an animal or culture supernatant by a known method.

In the present invention, the substance to be measured includes the at least three types of substances having different structures, and the first binding substances include the at least three types of binding substances which are capable of binding to the at least three types of substances having different structures, respectively.

For example, in a case where the substance to be measured is the bile acid, as the first binding substance, an anti-bile acid antibody that is capable of binding to the bile acids of a non-conjugate and a conjugate (preferably, specifically recognizes the bile acids) is used. Since the bile acids include the cholic acid, the deoxycholic acid, the chenodeoxycholic acid, and/or a conjugate thereof, in the present invention, as the first binding substance, an anti-cholic acid antibody, an anti-deoxycholic acid antibody, and an anti-chenodeoxycholic acid antibody can be produced so as to be used as the three types of antibodies.

As a specific method for producing the anti-cholic acid antibody, the anti-deoxycholic acid antibody, and the anti-chenodeoxycholic acid antibody, which react to the both non-conjugate and conjugate, a method for producing the anti-cholic acid antibody will be described below as an example.

By mixing a cholic acid, bovine serum albumin (hereinafter will be abbreviated as BSA), and a condensing agent, it is possible to produce a cholic acid-BSA conjugate in which a carboxylic acid moiety of the cholic acid has bind to BSA. The conjugate is used as a mouse immunizing antigen and a mouse is immunized subcutaneously several times on the back thereof. In this case, a complete adjuvant (Freund's Complete Adjuvant: FCA), and/or an incomplete adjuvant (Freund's Incomplete Adjuvant: FIA) can be appropriately selected and mixed with the immunizing antigen so as to be used. The complete adjuvant is a substance that stimulates immunity and is a mixture of paraffin and ARLACEL. The incomplete adjuvant is an adjuvant in which killed bacteria of dead mycobacteria or *Mycobacterium tuberculosis* are added to the complete adjuvant so as to further enhance antigenicity. After performing the immunization as appropriate for several times over several weeks, blood is collected from the mouse and antibody titers are measured. In a case where a sufficient increase in the antibody titers is observed, the antigen is administered intraperitoneally and the spleen is extracted several days later. By fusing the spleen cells extracted from the immunized mouse with mutant myeloma cell lines (myeloma), it is possible to produce hybrid cells having an antibody-producing ability. Among these hybrid cells, only cells producing an antibody against the target antigen are selected and subjected to limiting dilution so as to proliferate only the cell line thereof. Culturing (cloning) of the cells after dilution can be carried out. By intraperitoneally injecting the hybrid cell line obtained as above into the mouse so as to proliferate the ascites-type antibody-producing cells, it is possible to produce monoclonal antibodies in the ascites, and by recovering these antibodies, the target antibody can be obtained.

(Fluorescent Particle)

As the fluorescent particle used in the present invention, colored fluorescent particles which can be generally used for immunologic response can be used, and for example, fluorescent polymer particles such as fluorescent polystyrene beads, or fluorescent glass particles such as fluorescent glass beads can be used. Specific examples of a material of the fluorescent particles include synthetic polymer powders such as a polymer using a monomer such as styrene, methacrylic acid, glycidyl (meth)acrylate, butadiene, vinyl chloride, vinyl acetate acrylate, methyl methacrylate, ethyl methacrylate, phenyl methacrylate, or butyl methacrylate, or a copolymer using two or more kinds of monomers, and a latex in which these powders are uniformly suspended is preferred. In addition, other examples thereof include organic polymer powders and inorganic substance powders, microorganisms, blood cells and cell membrane pieces, liposomes, and the like.

In a case of using latex particles, specific examples of a material of the latex include polystyrene, styrene-acrylic acid copolymer, styrene-methacrylic acid copolymer, styrene-glycidyl (meth)acrylate copolymer, styrene-styrene sulfonic acid salt copolymer, methacrylic acid polymer, acrylic acid polymer, acrylonitrile-butadiene-styrene copolymer, vinyl chloride-acrylic acid ester copolymer, polyvinyl acetate acrylate, and the like. As the latex, a copolymer containing at least styrene as a monomer is preferable, and a copolymer of styrene and an acrylic acid or a methacrylic acid is particularly preferable. A method for producing the latex is not particularly limited, and the latex can be producing by any polymerization method. It is difficult to immobilize the antibody in a case where a surfactant is present in a case of antibody labeling, and therefore the production of the latex is preferably carried out by emulsion polymerization of a demulsifier, that is, emulsion polymerization without using an emulsifier such as a surfactant.

When the latex itself obtained by the polymerization is fluorescent, the latex can be used as the fluorescent latex particle as it is. In a case where the latex obtained by the polymerization is nonfluorescent, the fluorescent latex particle can be produced by adding a fluorescent substance (such as a fluorescent dye) to the latex. That is, the fluorescent latex particle can be produced by adding the fluorescent dye to a solution of latex particles containing water and a water-soluble organic solvent and stirring the same.

Liposomes, microcapsules, or the like which contain the fluorescent dye can also be used as the fluorescent particles. Fluorescence coloring is not particularly limited as long as the fluorescence coloring is released in a case of absorbing and exciting ultraviolet light or the like and returning to a ground state. For example, the fluorescence coloring such as yellow green (excitation wavelength 505 nm/emission wavelength 515 nm, hereinafter the same applies), blue (350 to 356 nm/415 to 440 nm), red (535 to 580 nm/575 to 605 nm), orange (540 nm/560 nm), red orange (565 nm/580 nm), crimson (625 nm/645 nm), dark red (660 nm/680 nm), and the like, may be used. These fluorescent particles emitting fluorescence are available from, for example, Thermo Fisher and are commercially available on the market under the trade name of FluoSpheres (registered trademark) of the same company.

An average particle diameter of the fluorescent particles varies depending on the material of the particles, a concentration range for the quantitative determination of the substance to be measured, a measuring instrument, and the like, but is preferably within the range of 0.001 to 10 μm (more preferably 0.001 to 1 μm).

(Method for Measuring Average Particle Diameter)

The average particle diameter of the fluorescent particles can be measured with a commercially available particle size distribution meter or the like. As a method for measuring the particle size distribution, optical microscopy, confocal laser microscopy, electron microscopy, atomic force microscopy, static light scattering method, laser diffraction method, dynamic light scattering method, centrifugal sedimentation method, electric pulse measurement method, chromatography method, ultrasonic attenuation method, and the like are known, and devices corresponding to the respective principles are commercially available.

From the viewpoint of the particle size range and the ease of measurement, it is preferable to use the dynamic light scattering method in the present invention. Commercially available determination devices using dynamic light scattering include NANOTRAC UPA (Nikkiso Co., Ltd.), dynamic light scattering type particle size distribution determination device LB-550 (Horiba Seisakusho), concentrated system particle size analyzer FPAR-1000 (Otsuka Electronics Co., Ltd.), ZETASIZER Nano series (Malvern Instruments Inc.), and the like, and in the present invention, a median diameter (d=50) measured at a measuring temperature of 25° C. is obtained.

(First Binding Substance on Surface of Fluorescent Particle)

It is preferable that the three or more types of the binding substances used as the first binding substances are used by being adsorbed to the surface of each fluorescent latex particle. In this aspect, one fluorescent particle of the fluorescent particles to be used has the above three types of the binding substances. Alternatively, an aspect in which a fluorescent latex particle to which one type (for example, the anti-cholic acid antibody) among the three or more types of the binding substances is adsorbed, a fluorescent latex particle to which another one (for example, the anti-deoxycholic acid antibody) among the three or more types of the binding substances is adsorbed, and a fluorescent latex particle to which the other one type (for example, the anti-chenodeoxycholic acid antibody) among the three or more types of the binding substances is adsorbed, is produced respectively so as to use a mixture of the above three types of the fluorescent latex particle, is also preferable.

In the present invention, the aspect in which the three or more types of the binding substances used as the first binding substance are used by being adsorbed to the surface of the one fluorescent particle (each fluorescent particle), is more preferable. In a case where the substance to be measured is aggregate of a plurality of different substances, it is preferable to use the fluorescent particles having all the binding substances to which each different substance binds. As one embodiment of the present invention, in the case where the substance to be measured is the bile acid, the fluorescent particles having all of the anti-cholic acid antibody, the anti-deoxycholic acid antibody, and the anti-chenodeoxycholic acid antibody can be used. With the above configuration, it becomes possible that all fluorescent particles interact with all of the substances to be measured composed of different substances present in a biological sample. Therefore, it is preferable that the at least three types of the binding substances bind to each fluorescent particle.

(Modification of Fluorescent Particles with First Binding Substance)

A method for immobilizing the first binding substance on the fluorescent particle is described in protocols and the like attached to, for example, JP2000-206115A and FluoSpheres (registered trademark) polystyrene microsphere F8813 manufactured by Thermo Fisher, and any known methods for preparing a reagent for immunoagglutination reaction can be used. In addition, as a principle of immobilizing an antibody as a binding substance to particles, any principle of physical adsorption and chemical bond by covalent bond can be adopted. As a blocking agent which covers the surface of the particle not coated with the antibody after the antibody is immobilized on the particles, it is possible to use a commercially available blocking agent for immunologic response, which contains the above-described substances or substances having the same properties as the above-described substance, which are known substances such as BSA, skim milk, casein, soy-derived components, fish-derived components, polyethylene glycol, and the like. These blocking agents can also be subjected to a pretreatment such as partial denaturation by heat, acid, alkali, or the like, as necessary.

Specific methods for immobilizing the antibody to particles are exemplified below. An antibody solution adjusted to have a concentration of 0.01 to 20 mg/mL is added to and mixed with a solution in which the particles are dispersed so that a concentration of solid contents of the particles becomes 0.1% to 10% by mass. The mixture is continuously stirred for 5 minutes to 48 hours under a temperature of 4° C. to 50° C. Subsequently, the particles and the solution are dissociated from each other by centrifugation or other methods so as to sufficiently remove the antibody which has not bind to the particles contained in the solution. Thereafter, the operation of washing the particles with a buffer solution is repeated 0 to 10 times. After carrying out the operation of mixing the particles with the antibody and allowing the antibody to bind to the particles, it is desirable to protect a portion of the particle surface to which the antibody has not bind by using a blocking agent such as components not involved in antigen-antibody reaction, preferably proteins, more preferably BSA, BLOCK ACE (registered trademark), skim milk, and casein.

In a case of immobilizing antigens, antibodies, and the like to particles, stabilizers can be added as necessary. The stabilizer is not particularly limited as long as the stabilizer stabilizes antigens and antibodies, such as synthetic polymers such as sucrose and polysaccharides, or natural polymers. Commercially available stabilizers such as Immunoassay Stabilizer (Advanced Biotechnologies Inc. (ABI)), and the like can also be used.

The fluorescent particles having the first binding substance are included in the kit of the present invention, and an aspect in which the fluorescent particles are contained in the container which is a part of the kit, for example, in a cup, is preferable. In this case, the biological sample is injected into the container containing the fluorescent particles, mixed, and stirred, whereby the first binding substance and the substance to be measured in the biological sample can bind to each other.

(Substrate)

In the present invention, in order to achieve highly sensitive measurement, it is preferable to adopt a measurement method that performs surface plasmon fluorescence (SPF) detection to be described below. As a substrate in this case, it is preferable to use a substrate having a metal film on a surface thereof. A metal constituting the metal film is not particularly limited as long as it is a metal by which surface plasmon resonance can occur. Preferable examples thereof include free electron metals such as gold, silver, copper, aluminum, or platinum, and gold is particularly preferable. In a case where gold is used, a detection region to be described below becomes a gold film surface. These metals can be used alone or in combination. Furthermore, in consideration of adhesion to the substrate, an intermediacy layer made of chromium or the like may be provided between the substrate and a layer formed of the metal. Any thickness of the metal film may be used, but is preferably, for example, 1 nm to 500 nm, and particularly preferably 10 nm to 200 nm. In a case where the thickness exceeds 500 nm, the surface plasmon phenomenon of a medium cannot be sufficiently detected. In addition, in a case of providing the intermediacy layer made of chromium or the like, the thickness of the intermediacy layer is preferably 0.1 nm to 10 nm.

The formation of the metal film may be carried out by a general method and can be carried out by, for example, a sputtering method, a vapor deposition method, an ion plating method, an electroplating method, an electroless plating method, or the like, but in order to improve the adhesiveness of the metal film by providing a mix layer of the substrate material and the metal film, it is preferable to produce the metal film by the sputtering method. In this case, a thickness of the mix layer of the substrate material and the metal film is not particularly limited as long as sufficient adhesiveness can be secured, but is preferably 10 nm or less.

The metal film is preferably disposed on the substrate. The term "disposed on the substrate" means not only that the metal film is disposed in direct contact with the substrate, but also that the metal film is disposed via other layers without in direct contact with the substrate. As a material of the substrate which can be used in the present invention, for example, optical glass such as BK7 (borosilicate glass) which is one of general optical glasses, or synthetic resin, specifically, polymethyl methacrylate, polyethylene terephthalate, polycarbonate, cycloolefin polymer, or the like which is transparent to laser light can be used. It is desirable that such a substrate has a material which does not exhibit anisotropy with respect to polarized light and has excellent workability.

As a preferred aspect of the substrate for detecting SPF, there is a substrate obtained by vapor-depositing a gold film on polymethyl methacrylate (PMMA), and the like.

The substrate has a detection region having a second binding substance capable of binding to any one of the substance to be measured and the first binding substance.

(Second Binding Substance)

The second binding substance is a substance capable of binding to the substance to be measured or is a substance capable of binding to the first binding substance. In a case where the quantitative determination is carried out by a sandwich assay method, the substance capable of binding to the substance to be measured can be used as the second binding substance. In a case where the quantitative determination is carried out by a competitive method, the substance capable of binding to the first binding substance can be used as the second binding substance. In the present invention, it is preferable to carry out the quantitative determination by a competitive method, and it is preferable to use the substance capable of binding to the first binding substance as the second binding substance.

The second binding substance is not particularly limited, but preferable examples thereof include an antigen, an antibody, or a complex thereof. The second binding substance is preferably an antigen, and the substance to be measured (which is the substance capable of binding to the first binding substances) is particularly preferably used as the second binding substance.

In a case where the substance to be measured is used as the second binding substance, the second binding substance is preferably at least three types of substances having different structures which are the substances to be measured, or a conjugate of the above three types of substances having different structures and a carrier. The term "carrier" means a substance to which a plurality of molecules of at least three types of substances to be measured can bind. A preferable second binding substance is an aspect including at least three types of conjugates in which a plurality molecules of the same type of substances to be measured bind to one molecule carrier. Preferable examples of the carrier include proteins and the like, and specific examples include bovine serum albumin.

In a case where the substances to be measured are the bile acids, it is preferable the second binding substance includes a cholic acid and/or a cholic acid-albumin conjugate, a deoxycholic acid and/or a deoxycholic acid-albumin conjugate, and a chenodeoxycholic acid and/or a chenodeoxycholic acid-albumin conjugate. Alternatively, in the above-described aspects, an aspect in which a cholic acid conjugate is contained in a cholic acid, an aspect in which a cholic acid is substituted with a cholic acid conjugate, an aspect in which a deoxycholic acid conjugate is contained in a deoxycholic acid, an aspect in which a deoxycholic acid is substituted with a deoxycholic acid conjugate, an aspect in which a chenodeoxycholic acid conjugate in contained in a chenodeoxycholic acid, or an aspect in which a chenodeoxycholic acid is substituted with a chenodeoxycholic acid conjugate, is preferable. It is particularly preferable to include a cholic acid and/or a cholic acid-albumin conjugate, a deoxycholic acid and/or a deoxycholic acid-albumin conjugate, and a chenodeoxycholic acid and/or a chenodeoxycholic acid-albumin conjugate.

(Method for Immobilizing Second Binding Substance on Substrate)

A method for immobilizing the second binding substance on the substrate is described in, for example, Tech Notes Vol. 2-12 and the like provided by Nunc, and any known methods for preparing a general ELISA (Enzyme-Linked ImmunoSorbent Assay) reagent can be used. In addition, surface modification may be performed by disposing a self-assembled monolayer (self-assembled monolayer: SAM) or the like on the substrate, and any method of a method using physical adsorption and a method using chemical bonds by covalent bonds can be adopted as a method for immobilizing the second binding substance on the substrate. As a blocking agent which covers the surface of the substrate not coated with the second binding substance after the second binding substance is immobilized on the substrate, it is possible to use a commercially available blocking agent for immunologic response, which contains the above-described substances or substances having the same properties as the above-described substance, which are known substances such as BSA, skim milk, casein, soy-derived components, fish-derived components, polyethylene glycol, and the like. These blocking agents can also be subjected to a pretreatment such as partial denaturation by heat, acid, alkali, or the like, as necessary.

(Detection Region <Test Area>)

In the present invention, a test area for detecting the presence or absence of the substance to be measured in the biological sample can be provided on the substrate. In this test area, it is possible to quantitatively determine antigens by, for example, capturing the antigens which are the substances to be measured, and detecting and quantitatively determining an amount of label bound to the antigens. Alternatively, it is possible to quantitatively determine the antigens by a method of preventing only a label bound to the antigens from binding, capturing only a label not bound to the antigens, and calculating an amount of label bound to the antigens. This detection method is called a competitive method, and the substrate relating to the competitive method will be explained.

In the test area of the substrate, it is preferable to provide sites reacting with all the three or more types of binding substances (for example, antibodies) present on the fluorescent particles. As a preferable aspect of the present invention, an aspect in which three or more types of antigens present in the biological sample are provided on the test area of the substrate is preferable. In this case, it is possible to produce the test area by reacting the antigens with BSA in the presence of a condensing agent to produce an antigen-BSA conjugate and adsorbing this conjugate on the test area. Therefore, in the aspect, on the test area, the BSA conjugate combined with the three or more types of antigens coexists in one area. In this case, it is preferable that the three types of antigens-BSA conjugates are randomly mixed so as to be disposed on the test area. It is possible that the antigen-BSA conjugate is dissolved in a buffer solution, spotted onto the substrate, and left alone for a certain period of time, and then the supernatant is aspirated and bound to the test area on the substrate by a method such as drying.

(Reference Region <Control Area>)

In the present invention, in order to minimize the influence of the measurement environment, particularly the measurement temperature, a control area is provided on the substrate and information of the test area is standardized by information of the control area, and therefore it is possible to suppress environment dependency to a significantly low level. It is preferable that the control area is designed such that the control area can be combined with all the labels irrespective of an amount of the substances to be measured which are present in the biological sample to be used. It is preferable that an antibody which interacts with all the three or more types of antibodies present on the fluorescent particles which are labels, is provided. With such a design, by standardizing the information of the test area with the information of the control area, even in a case where the flow of the biological sample or the reaction rate is influenced by, for example, a low temperature environment, it is possible to cancel the influence by standardization and to obtain a result which is not influenced by the measurement environment with high accuracy at all cases.

As a preferable antibody to be present in the control area, an anti-mouse antibody is preferable as long as an anti-mouse antibody has a function of recognizing the three or more types of the binding substances (for example, antibodies) present on the fluorescent particles and is derived from a mouse, and in a case where the antibody on the fluorescent particle is derived from a goat, an anti-goat antibody is preferable. It is possible that these antibodies on the control area are dissolved in a buffer solution, spotted onto the substrate, and left alone for a certain period of time, and then the supernatant is aspirated and bound to the substrate by a method such as drying.

(Nonspecific Adsorption Preventing Substance)

In the reagent kit of the present invention, it is preferable to further modify the fluorescent particles with a substance which does not specifically bind to the substances to be measured or with the binding substance. For example, in the competitive method, not only a negative biological sample that does not contain the substances to be measured, but also a biological sample that also reacts to a positive biological sample containing the substances to be measured so as to become negative, exists, and a solution to a high value dissociation problem is recognized as an object. Although the cause of such false negative is not clarified, it is considered that the presence of the fluorescent particle, which is not to be bound, due to nonspecific interaction between the surface of the fluorescent particle not covered with the antibody and the detection region (test area), is one of the reasons. In addition, even in a case where the same substance as the substance present on the test area is present on the surface of the fluorescent particle, in a case where a liberated antibody or the like is present in the biological sample, there is a case in which this antibody binds to any one of the substance present on the test area and the substance on the surface of the fluorescent particle, and thus a case in which a positive biological sample containing the substances to be measured is measured, is also detected as negative. In general, blocking with BSA is used for suppressing nonspecific adsorption to a solid surface (for example, the surface of the fluorescent particle, a gold film surface of the substrate), but in a case where an anti-BSA antibody reacting with BSA is present in a specific biological sample, BSA on the fluorescent particle reacts with BSA on the substrate so as to be crosslinked, and high value dissociation occurs in some cases. Therefore, as a preferable binding substance, it is preferable to use a substance which does not specifically bind to the substances to be measured (for example, bile acids) and does not bind to a causative substance exhibiting false negative as described above. Antibodies that do not bind to the bile acids, proteins not to be used in the test area (Protein A, Protein G), or the like can be used as the binding substance, among which the antibodies that do not bind to the bile acids is preferable. Specifically, an antiserum prepared from blood serum of an animal immunized with an antigen different from bile acid, an immunoglobulin fraction purified from an antiserum, a monoclonal antibody obtained by cell fusion using spleen cells of an animal immunized with the substances to be measured, fragments thereof [for example, F(ab')$_2$, Fab, Fab', or Fv], and the like can be used. The preparation of these antibodies can be carried out by using a general method. Furthermore, an antibody modified as a case of a chimeric antibody or the like may be used, or a commercially available antibody also may be used as long as the antibody is an antibody prepared from blood serum of an animal or culture supernatant by a known method. In the present invention, an aspect in which an anti-CRP (C-reactive protein) antibody is used as the binding substance is particularly preferable.

(Antibody)

In the present invention, the antibody can be used regardless of animal species or subclass thereof. For example, the antibody that can be used in the present invention is an antibody derived from an organism in which an immunologic response can occur, such as mouse, rat, hamster, goat, rabbit, sheep, cow, and chicken. Specific examples thereof include mouse IgG, mouse IgM, rat IgG, rat IgM, hamster IgG, hamster IgM, rabbit IgG, rabbit IgM, goat IgG, goat IgM, sheep IgG, sheep IgM, bovine IgG, bovine IgM, avian IgY, and the like, and both polyclonal and monoclonal antibodies can be used. Fragmented antibodies are molecules derived from intact antibodies having at least one antigen binding site, and specific examples thereof include Fab, F(ab')$_2$ and the like. These fragmented antibodies are molecules obtained by enzymatic or chemical treatment or using genetic engineering techniques.

(Measurement Method)

According to the present invention, the biological sample is brought in contact with the fluorescent particles having the first binding substances capable of binding to the substances to be measured, in the substrate that has the detection region having the second binding substances capable of binding to any one of the substances to be measured and the first binding substances, and then fluorescence due to the fluorescent particles bound to the second binding substances of the detection region is measured, and therefore the substances to be measured in the biological sample can be quantitatively determined.

The quantitative determination in the present invention is interpreted as the broadest concept as long the quantitative determination is measurement of an amount of the substances to be measured (for example, bile acid). Specific aspects of the measurement method include the competitive method and the sandwich method, but the competitive method is preferable.

As an example of the competitive method, a case of quantitatively determining bile acids is described below. A case of quantitatively determining substances other than bile acids, can also be carried out in the same manner.

In the competitive method, first, in a bile acid immunoassay substrate on which a bile acid-albumin conjugate having a bile acid/albumin ratio of 7 to 14 is immobilized, the biological sample containing the bile acid is contacted with an anti-bile acid antibody-labeled fluorescent particle. In a case where the bile acid is not present in the biological sample, an antigen-antibody reaction occurs on the substrate by the anti-bile acid antibody-labeled fluorescent particle and the bile acid on the substrate (that is, the bile acid in the bile acid-albumin conjugate). On the other hand, in a case where the bile acid is present in the biological sample, an antigen-antibody reaction occurs between the bile acid in the biological sample and the anti-bile acid antibody-labeled fluorescent particle, and an antigen-antibody reaction is inhibited between the bile acid (for example, the bile acid in the bile acid-albumin conjugate) on the substrate and the anti-bile acid antibody-labeled fluorescent particle. After completion of the above reaction, anti-bile acid antibody-labeled fluorescent particles not bound to albumin on the substrate are removed. Subsequently, by detecting a degree of formation of immune complexes on the substrate (that is, a complex of the anti-bile acid antibody-labeled fluorescent particle and the bile acid in the bile acids-albumin conjugate on the substrate) as fluorescence intensity, it is possible to measure a concentration of the bile acid in the biological sample, and the like.

As a measurement form of fluorescence in the competitive method, it is possible to adopt any one of plate reader measurement and flow measurement, and for example, the measurement can be carried out by the following method. A plurality of samples with known amounts of the bile acid differing in bile acid concentration is prepared in advance, and this sample is mixed with the anti-bile acid antibody-labeled fluorescent particles in advance. This mixed solution is brought into contact with a region on which the bile acid-albumin conjugate is immobilized. A fluorescent signal from the region on which the bile acid-albumin conjugate is immobilized is measured as a plurality of fluorescent signals while the mixed solution is in contact with the conjugate at specific time intervals. Based on the plurality of fluorescent signals, a time change (inclination) of the amount of fluorescence is obtained at each bile acid concentration. By plotting this time change as a Y-axis and the bile acid concentration as an X-axis, a relational expression of the bile acid concentration with respect to the time change in the fluorescence amount is acquired by using an appropriate fitting method such as a least squares method or the like. Based on the relational expression thus obtained, the amount of bile acid contained in the biological sample can be quantitatively determined by using the result of the time change of the amount of fluorescence using the biological sample to be examined.

The quantitative determination of the amount of bile acid is preferably carried out in a short period of time. Specifically, the quantitative determination is preferably carried out within 10 minutes, more preferably within 8 minutes, and even more preferably within 6 minutes. By using the relational expression between the time change rate in the amount of fluorescence and the bile acid concentration acquired in advance using an appropriate fitting method such as the least squares method or the like, the sample and the anti-bile acid antibody-labeled fluorescent particle are brought into contact with the detection region to which the bile acid-albumin conjugate is immobilized, and then a time for converting the amount of bile acid contained in the biological sample is obtained based on the result of the time change of the fluorescence amount using the biological sample to be examined, and a time for the quantitative determination preferably includes this time for conversion.

The sandwich method is not particularly limited, and for example, the substances to be measured can be measured by the following procedure. A biological sample that may contain the substances to be measured and the fluorescent particle having the first binding substance capable of binding to the substances to be measured are brought into contact with each other on the substrate. In a case where the substances to be measured is present in the biological sample, a binding reaction (such as an antigen-antibody reaction) occurs between the substances to be measured, the fluorescent particle, and the substrate. As a result, in a case where the substances to be measured is present in the biological sample, an immune complex composed of the second binding substance bound to the substrate, the substances to be measured, and the fluorescent particles having the first binding substance is formed. In the sandwich method, after completion of the reaction between the second binding substance, the substances to be measured, and the fluorescent particle having the first binding substance, the fluorescent particle having the first binding substance, in which the immune complex has not been formed, is removed and washed. Subsequently, the concentration of substances to be measured or the like can be measured by detecting a degree of immune complex formation as fluorescence intensity. The fluorescence intensity and the concentration of substances to be measured have a positive correlation.

(Flow Passage)

In a preferable aspect of the present invention, a mixed solution obtained by mixing the biological sample that may contain the substances to be measured and the fluorescent particles having the first binding substance can be applied on the substrate and developed in a flow passage. The flow passage is not particularly limited as long as it is a passage that allows the biological sample and the fluorescent particle having the first binding substance to flow down to the detection region. Preferable aspects of the flow passage include a spotting port for spotting the biological sample solution containing the fluorescent particles having the first binding substance, the metal film as the detection region, and a flow passage beyond the metal film. The biological sample has a structure capable of passing over the metal film. Preferably, a suction port can be provided on the side opposite to the spotting port with respect to the metal film.

(Measurement of Surface Plasmon Fluorescence)

A method for detecting fluorescence in the present invention is not particularly limited, and examples thereof include a device capable of detecting fluorescence intensity. Specifically, it is preferable to detect fluorescence intensity using a microplate reader, or biosensor for performing fluorescence detection (SPF) by surface plasmon excitation. The form of measurement of fluorescence may be plate reader measurement or flow measurement. The fluorescence detection method (SPF method) by surface plasmon excitation can perform the measurement with higher sensitivity than the fluorescence detection method (epifluorescence method) by epi-excitation.

As a surface plasmon fluorescence (SPF) biosensor, for example, it is possible to use a sensor, which is described in JP2008-249361A, the sensor including an optical waveguide formed from a material that transmits excitation light of a predetermined wavelength, a metal film formed on one surface of this optical waveguide, a light source for generating a light beam, an optical system that allows the light beam to pass through the optical waveguide and causes the light beam to enter the interface between the optical waveguide and the metal film at an incident angle that generates surface plasmons, and a fluorescence detection means for detecting the fluorescence generated by being excited by the above-described evanescent wave enhanced by the surface plasmon.

The fluorescence detection (SPF) system by surface plasmon excitation using the fluorescent particles of the present invention is a preferably an assay method for detecting fluorescence from the fluorescent substance dependent on the amount of substances to be measured immobilized on the metal film on the substrate, which is the method different from a so-called latex agglutination method in which a change in optical transparency is detected as, for example, turbidity due to progress of reaction in a solution. In the latex agglutination method, an antibody-sensitized latex in the latex reagent and the antigen in the biological sample bind and aggregate by an antibody reaction. The latex agglutination method is a method in which the agglomerate increases with time, and an antigen concentration is quantitatively determined from a change in absorbance per unit time obtained by irradiating the aggregate with near infrared light. In the present invention, it is possible to provide a significantly simple method for detecting the substances to be measured as compared with the latex agglutination method.

(Other Components of Kit)

The kit of the present invention is used for the method for measuring the substances to be measured (for examples, bile acids), and is a kit for diagnosis of the bile acid measurement in a case where the substances to be measured are the bile acids. In a case of carrying out the measurement of the substances to be measured such as bile acids in the present invention, the sensor chip including a substrate on which the second binding substance such as a bile acid-albumin conjugate is immobilized; and a member for retaining the fluorescent particle, is provided, but various devices or instruments used for measuring the substances to be measured such as surface plasmon excitation devices and fluorescence measurement devices may be provided. Furthermore, as a component of the kit, a sample containing substances to be measured of known amounts, an instruction manual, and the like may be included.

The present invention will be more specifically described with reference to the following examples, but the present invention is not limited by the examples.

EXAMPLES (1) Preparation of Bile Acid-Bovine Serum Albumin Conjugate (1-1) Preparation of Cholic Acid-Bovine Serum Albumin Conjugate To 1.2 mL of super dehydrated dimethylformamide (hereinafter, will be referred to as DMF, manufactured by Wako Pure Chemical Industries, Ltd.), 50 mg of cholic acid (manufactured by Wako Pure Chemical Industries, Ltd.) and 67 mg of N-hydroxysuccinimide (hereinafter, will be referred to as NHS, manufactured by Wako Pure Chemical Industries, Ltd.), and 110 mg of 1-ethyl-3-(3-dimethylaminopropyl)carbodiimide (hereinafter, will be referred to as EDC, manufactured by Wako Pure Chemical Industries, Ltd.) were added so as to be mixed, and therefore a cholic acid was actively esterified. This actively esterified cholic acid was dropwise added to and reacted with an aqueous solution of a 65 mL of a phosphate buffer solution (hereinafter, will be referred to as PBS, manufactured by Wako Pure Chemical Industries, Ltd.) in which 322 mg of bovine serum albumin (hereinafter, will be referred to as BSA, manufactured by Wako Pure Chemical Industries, Ltd.) as one type of albumin was dissolved. After completion of the reaction, the reaction solution was purified by dialysis using 1 L of a solution in which a ratio of acetonitrile (hereinafter, will be referred to ACN, manufactured by Wako Pure Chemical Industries, Ltd.)/water was 1/3. Finally, freeze-drying was carried out, and therefore a white solid was obtained.

(1-2) Preparation of Deoxycholic Acid-BSA Conjugate 50 mg of deoxycholic acid (manufactured by Wako Pure Chemical Industries, Ltd.), 67 mg of NHS, and 110 mg of EDC were added to 1.2 mL of super dehydrated DMF so as to be mixed, and therefore the deoxycholic acid was actively esterified. This actively esterified deoxycholic acid was added dropwise to and reacted with an aqueous solution of 65 mL of PBS in which 322 mg of BSA was dissolved. After completion of the reaction, the reaction solution was purified by dialysis using 1 L of a solution in which a ratio of ACN/water was 1/3. Finally, freeze-drying was carried out, and therefore a white solid was obtained.

(1-3) Preparation of Chenodeoxycholic Acid-BSA Conjugate 50 mg of chenodeoxycholic acid (manufactured by Wako Pure Chemical Industries, Ltd.), 67 mg of NHS, and 110 mg of EDC were added to 1.2 mL of super dehydrated DMF so as to be mixed, and therefore the chenodeoxycholic acid was actively esterified. This actively esterified chenodeoxycholic acid was added dropwise to and reacted with an aqueous solution of 65 mL of PBS in which 322 mg of BSA was dissolved. After completion of the reaction, the reaction solution was purified by dialysis using 1 L of a solution in which a ratio of ACN/water was 1/3. Finally, freeze-drying was carried out, and therefore a white solid was obtained.

(2) Measurement of Mole Ratio of Bile Acid/BSA Label (Bile Acid/Albumin Ratio of Conjugate) by MALDI-TOF-MS (Matrix-Assisted Laser Desorption Ionization-Time of Flight Mass Spectrometry)

(Measurement Procedure)

The conjugates prepared in (1-1) to (1-3) were dissolved in a solution in which a ratio of 0.1% by mass of trifluoroacetic acid (TFA):ACN is 2:1, and a concentration was adjusted to 1 mg/mL. 1 μL of this solution and 4 μL of matrix (sinapinic acid: SA (manufactured by Wako Pure Chemical Industries, Ltd.)) were mixed and 4 points were spotted with 1 μL on a gold plate. After drying naturally, a gold plate was inserted into a MALDI-TOF-MS apparatus (Applied Bio Systems, Inc. Voyager), 900 shots were accumulated per spot, and therefore data as mass information was obtained (N=4). Using this data, a molecular weight center value at 50% intensity of a maximum value of the peak intensity of the peak corresponding to the bile acid-BSA conjugate was adopted as the peak of the BSA conjugate, and a point where the peak value was lowered vertically was set as a molecular weight of the bile acid-BSA conjugate so as to obtain an average value of N=4, and therefore the number of bile acids binding to BSA was calculated by (molecular weight of bile acid-BSA conjugate-molecular weight of native BSA)/molecular weight of bile acid (for example, in a case of cholic acid, 408-18=390). The bile acid/BSA ratio of the obtained conjugate is shown in Table 1.

TABLE 1

| Conjugate | Bile acid-BSA conjugate | Bile acid/BSA mole ratio |
|---|---|---|
| Conjugate-1 | Cholic acid-BSA | 13 |
| Conjugate-2 | Deoxycholic acid-BSA | 13 |
| Conjugate-3 | Chenodeoxycholic acid-BSA | 13 |

(3) Production of Hybridomas for Producing Cholic Acid Antibody, Deoxycholic Acid Antibody, or Chenodeoxycholic Acid Antibody, and Antibody Production (3-1) Immunogen 2 mg each of the cholic acid-BSA conjugate, the deoxycholic acid-BSA conjugate, and the chenodeoxycholic acid-BSA conjugate produced above was used as an immunogen for mouse immunization.

(3-2) Preparation of Hybridoma

As the immunogen for mouse immunization, the cholic acid-BSA conjugate was used.

The cholic acid-BSA conjugate was subcutaneously administered to a mouse so as to carry out the immunization by an initial immunization with an amount of 100 μg/mouse, and a second and subsequent immunizations with an amount of 50 μg/mouse. In the immunization, an emulsion mixed with complete adjuvant (FCA) was administered first, and for the second to fourth immunizations, an emulsion mixed with incomplete adjuvant (FIA) was administered. The immunizations were carried out 4 times at 2-week interval. Separately, blood was collected the following week of the third and fourth immunizations, and antibody titers were measured by ELISA measurement using 100 μL of the collected serum. It was confirmed that the antibody titers were the target values, and the conjugate as an antigen was diluted and dissolved in 1 mL of a phosphate buffer solution (PBS, manufactured by Wako Pure Chemical Industries, Ltd., pH 7.1 to 7.3) and the resultant was intraperitoneally administered to a mouse, while taking the immunization two weeks after the fourth immunization as a final immunization. The spleen of the mouse was extracted 3 days after the administration.

Spleen cells extracted from the mouse and mutant myeloma cell lines (myeloma: P3-X63-Ag8-U1) were mixed at a ratio of 7:1 of the number of cells, and then polyethylene glycol (PEG) was added thereto. After centrifugation, the cells were suspended in a medium (RPMI-1640 (Roswell Park Memorial Institute Medium)+10% by mass fetal bovine serum (FBS)). The suspended spleen cells were seeded on a 96-well plate so that the number of cells was 1.0×10exp5 (cell/well). On the next day, HAT medium (hypoxanthine-aminopterin-thymidine medium) was added thereto and the culture supernatant of the proliferated hybridomas was screened by ELISA of the antibody assay system. The cholic acid-BSA conjugate, which is an antigen for measurement, was diluted with PBS to a concentration of 500 ng/mL, added to a cup of ELISA and left alone, and then immobilized at the bottom of the cup so as to remove the supernatant. An anti-mouse IgG HRP-labeled antibody was used as a secondary antibody against the antibody produced by the spleen cells of the measurement target. IgG shows immunoglobulin G and HRP shows horseradish peroxidase. Wells positive from the results of ELISA were cultured using a 24-well plate, and 1 mL of each culture supernatant was collected. Secondary screening was performed again by the same antibody assay system ELISA. In the same well at the time of cell fusion, the top 6 wells having high ELISA signals were selected and put in a vial.

The cells in each vial were subjected to limiting dilution using basal medium RPMI 1640 containing 10% by mass of FBS, and therefore dilutions were prepared. One drop of each dilution was pipetted and added into each well of six 96-well plates. Each well was observed under a microscope, and it was confirmed that the cells in each well were single cells. After culturing for 3 weeks, culture supernatants of the proliferated hybridomas were screened by ELISA of the antibody assay system in the same manner as described above. The top 10 wells with high ELISA signals were selected and hybridoma preparation was completed. An Isotyping kit (manufactured by Roche) was used to determine the subclass of the obtained antibody.

(3-3) Production of Antibody by Mouse Ascites Method

In the same manner, cells selected from the 10 wells were subjected to ELISA screening, and antibodies were produced by a mouse ascites method (using two mice) with respect to the top cells of the wells having a highest signal. The obtained antibody is referred to as an anti-cholic acid antibody-1.

(3-4) Preparation of Deoxycholic Acid Antibody and Chenodeoxycholic Acid Antibody The preparation of a deoxycholic acid antibody and a chenodeoxycholic acid antibody was carried out in the same manner as above. The obtained antibodies are referred to as an anti-deoxycholic acid antibody-1 and an anti-chenodeoxycholic acid antibody-1, respectively.

(3-5) Subclass of Antibody and Antibody Production

The subclass of the antibodies prepared above and an antibody production amount are shown in Table 2.

TABLE 2

Subclass and Antibody Production Amount

| Antibody | Subclass | Antibody production amount by mouse ascites method (2 mice) |
|---|---|---|
| Anti-cholic acid antibody-1 | IgG1 | 10.0 mg |
| Anti-deoxycholic acid antibody-1 | IgG1 | 28.7 mg |
| Anti-chenodeoxycholic acid antibody-1 | IgG1 | 30.4 mg |

(4) Production of Anti-Mouse Antibody

A mouse-derived globulin (LAMPIRE Biological Laboratories, Catalog No. 7404302, Mouse Gamma Globulin Salt Fractionation, 500 mg) was prepared, and the immunization of goats (subcutaneous immunization) was carried out four times at two-week intervals by using the method in which the emulsion mixed with complete adjuvant (FCA) was administered first and for the second to fourth immunizations, the emulsion mixed with incomplete adjuvant (FIA) was administered. Thereafter, ELISA measurement was carried out to confirm an increase in antibody titers, followed by performing of total blood collection, and antiserum was obtained by centrifugation. Thereafter, purification was carried out using Protein A column (Pierce Protein A Columns, catalog No. 20356, manufactured by Thermo scientific Co., Ltd.), and therefore a desired anti-mouse antibody was obtained.

(5) Production of Anti-CRP Antibody

Commercially available human CRP (manufactured by Kitayama Labes Co., Ltd.) was prepared, and the immunization of mice (subcutaneous immunization) was carried out four times at two-week intervals by using the method in which the emulsion mixed with complete adjuvant (CFA) was administered first and for the second to fourth immunizations, the emulsion mixed with incomplete adjuvant (IFA) was administered. Thereafter, ELISA measurement was carried out to confirm an increase in antibody titers, followed by performing of total blood collection, and antiserum was obtained by centrifugation. Thereafter, purification was carried out using Protein A column (Pierce Protein A Columns, catalog No. 20356, manufactured by Thermo scientific Co., Ltd.), and therefore a desired anti-CRP antibody 1 was obtained.

(6) Preparation of Fluorescent Particles Labeled with Anti-Bile Acid Antibody (6-1) Preparation of Fluorescent Particle 1 to which Three Types of Anti-Bile Acid Antibodies are Adsorbed Fluorescent particles labeled with three anti-bile acid antibodies were prepared as follows.

282 µL buffer solution (pH 6.0) with MES (2-morpholinoethanesulfonic acid) of 50 mmol/L was added to 357 µL aqueous solution with the fluorescent latex particle of 2% by mass (concentration of solid contents) (manufactured by Invitrogen, average particle size 200 nm), 5.3 µL with the anti-cholic acid antibody-1 of 5 mg/mL (produced above), 5.3 µL with the anti-deoxycholic acid antibody-1 of 5 mg/mL (produced above), 6.9 µL with the anti-chenodeoxycholic acid antibody-1 of 5 mg/mL (produced above), and 75.5 µL with the anti-CRP antibody-1 of 5 mg/mL (dummy) (produced above) were added thereto and stirred at room temperature for 15 minutes. Thereafter, 7.5 µL aqueous solution with EDC of 10 mg/mL was added thereto, and the mixture was stirred at room temperature for 1.5 hours. 37.5 µL aqueous solution with Glycine of 2 mol/L (manufactured by Wako Pure Chemical Industries, Ltd.) was added thereto and stirred for 15 minutes, followed by centrifugation (15,000 rpm, 4° C., 15 minutes) so as to precipitate fluorescent latex particles. rpm indicates revolution per minute, and 1 rpm=1 min$^{-1}$. Thereafter, the supernatant was removed, 750 µL PBS (pH 7.4) was added, and fluorescent latex particles were redispersed with an ultrasonic washer. The centrifugation (15,000 rpm, 4° C., 15 minutes) was carried out again so as to remove the supernatant, then 750 µL PBS (pH 7.4) containing BSA of 1% by mass was added thereto so as to redisperse the fluorescent latex particles, and therefore a solution with the fluorescent latex particles of 1% by mass to which three types of the anti-bile acid antibodies and the anti-CRP antibody bound, was prepared.

(6-2) Preparation of Fluorescent Particle 2 to which Only Anti-Cholic Acid Antibody is Adsorbed 282 µL buffer solution (pH 6.0) with MES of 50 mmol/L was added to 357 µL aqueous solution with the fluorescent latex particles of 2% by mass (concentration of solid contents) (manufactured by Invitrogen Corporation, average particle size 200 nm), 201 µL with the anti-cholic acid monoclonal antibody-1 of 5 mg/mL (produced as above) was added thereto, and the mixture was stirred at room temperature for 15 minutes. Thereafter, 7.5 µL aqueous solution with EDC of 10 mg/mL was added thereto, and the mixture was stirred at room temperature for 1.5 hours. 37.5 µL aqueous solution with Glycine of 2 mol/L (manufactured by Wako Pure Chemical Industries, Ltd.) was added thereto and stirred for 15 minutes, followed by centrifugation (15,000 rpm, 4° C., 15 minutes) so as to precipitate fluorescent latex particles. Thereafter, the supernatant was removed, 750 µL PBS (pH 7.4) was added, and fluorescent latex particles were redispersed with an ultrasonic washer. The centrifugation (15,000 rpm, 4° C., 15 minutes) was carried out again so as to remove the supernatant, then 750 µL PBS (pH 7.4) containing BSA of 1% by mass was added thereto so as to redisperse the fluorescent latex particles, and therefore a solution with the fluorescent latex particles of 1% by mass to which one type of the anti-cholic acid antibody bound, was prepared.

(6-3) Preparation of Fluorescent Particle 3 to which Only Anti-Deoxycholic Acid Antibody is Adsorbed 282 µL buffer solution (pH 6.0) with MES of 50 mmol/L was added to 357 µL aqueous solution with the fluorescent latex particles of 2% by mass (concentration of solid contents) (manufactured by Invitrogen Corporation, average particle size 200 nm), 201 µL with the anti-deoxycholic acid monoclonal antibody-1 of 5 mg/mL (produced as above) was added thereto, and the mixture was stirred at room temperature for 15 minutes. Thereafter, 7.5 µL aqueous solution with EDC of 10 mg/mL was added thereto, and the mixture was stirred at room temperature for 1.5 hours. 37.5 µL aqueous solution with Glycine of 2 mol/L (manufactured by Wako Pure Chemical Industries, Ltd.) was added thereto and stirred for 15 minutes, followed by centrifugation (15,000 rpm, 4° C., 15 minutes) so as to precipitate fluorescent latex particles. Thereafter, the supernatant was removed, 750 µL PBS (pH 7.4) was added, and fluorescent latex particles were redispersed with an ultrasonic washer. The centrifugation (15,000 rpm, 4° C., 15 minutes) was carried out again so as to remove the supernatant, then 750 µL PBS (pH 7.4) containing BSA of 1% by mass was added thereto so as to redisperse the fluorescent latex particles, and therefore a solution with the fluorescent latex particles of 1% by mass to which one type of the anti-deoxycholic acid antibody bound, was prepared.

(6-4) Preparation of Fluorescent Particle 4 to which Only Anti-Chenodeoxycholic Acid Antibody is Adsorbed 282 µL buffer solution (pH 6.0) with MES of 50 mmol/L was added to 357 µL aqueous solution with the fluorescent latex particles of 2% by mass (concentration of solid contents) (manufactured by Invitrogen Corporation, average particle size 200 nm), 201 µL with the anti-chenodeoxy-cholic acid monoclonal antibody of 5 mg/mL (produced as above) was added thereto, and the mixture was stirred at room temperature for 15 minutes. Thereafter, 7.5 µL aqueous solution with EDC of 10 mg/mL was added thereto, and the mixture was stirred at room temperature for 1.5 hours. 37.5 µL aqueous solution with Glycine of 2 mol/L (manufactured by Wako Pure Chemical Industries, Ltd.) was added thereto and stirred for 15 minutes, followed by centrifugation (15,000 rpm, 4° C., 15 minutes) so as to precipitate fluorescent latex particles. Thereafter, the supernatant was removed, 750 µL PBS (pH 7.4) was added, and fluorescent latex particles were redispersed with an ultrasonic washer. The centrifugation (15,000 rpm, 4° C., 15 minutes) was carried out again so as to remove the supernatant, then 750 µL PBS (pH 7.4) containing BSA of 1% by mass was added thereto so as to redisperse the fluorescent latex particles, and therefore a solution with the fluorescent latex particles of 1% by mass to which one type of the anti-chenodeoxycholic acid antibody bound, was prepared.

(7) Production of Substrate

Polymethyl methacrylate (PMMA) substrate (ACRYPET (registered trademark) VH, manufactured by Mitsubishi Rayon Co., Ltd.) was prepared. By a magnetron sputtering method, a gold film with a thickness of 45 nm was produced on one side of two regions of a detection region and a reference region so that a width became 4 mm and a length became 3 mm, and was used as a chip constituting the substrate. A solution (concentration: 50 µg/mL in 50 mmol/L MES buffer solution, pH 6, 150 mmol/L NaCl) containing the conjugate 1, the conjugate 2, and the conjugate 3 by a content ratio (mass ratio 1:1:1) was spotted on the gold film surface of the detection region of the chip and dried, and therefore a plurality of substrates 1 on which the three types of the conjugates were immobilized were produced. In addition, the solution (concentration: 50 µg/mL in 50 mmol/L MES buffer solution, pH 6, 150 mmol/L NaCl) containing the anti-mouse antibody produced in (4) was spotted on the reference region of each substrate and dried.

Before using the three types of plurality of substrates prepared as above as a flow passage of the sensor chip, the substrates were repeatedly washed 3 times using 300 µL of a cleaning solution prepared in advance (PBS (pH 7.4) containing TWEEN 20 (POLYOXYETHYLENE (20) SORBITAN MONOLAURATE manufactured by Wako Pure Chemical Industries, Ltd.) of 0.05% by mass).

(8) Production of Flow Passage-Type Sensor Chip

Figure 1:
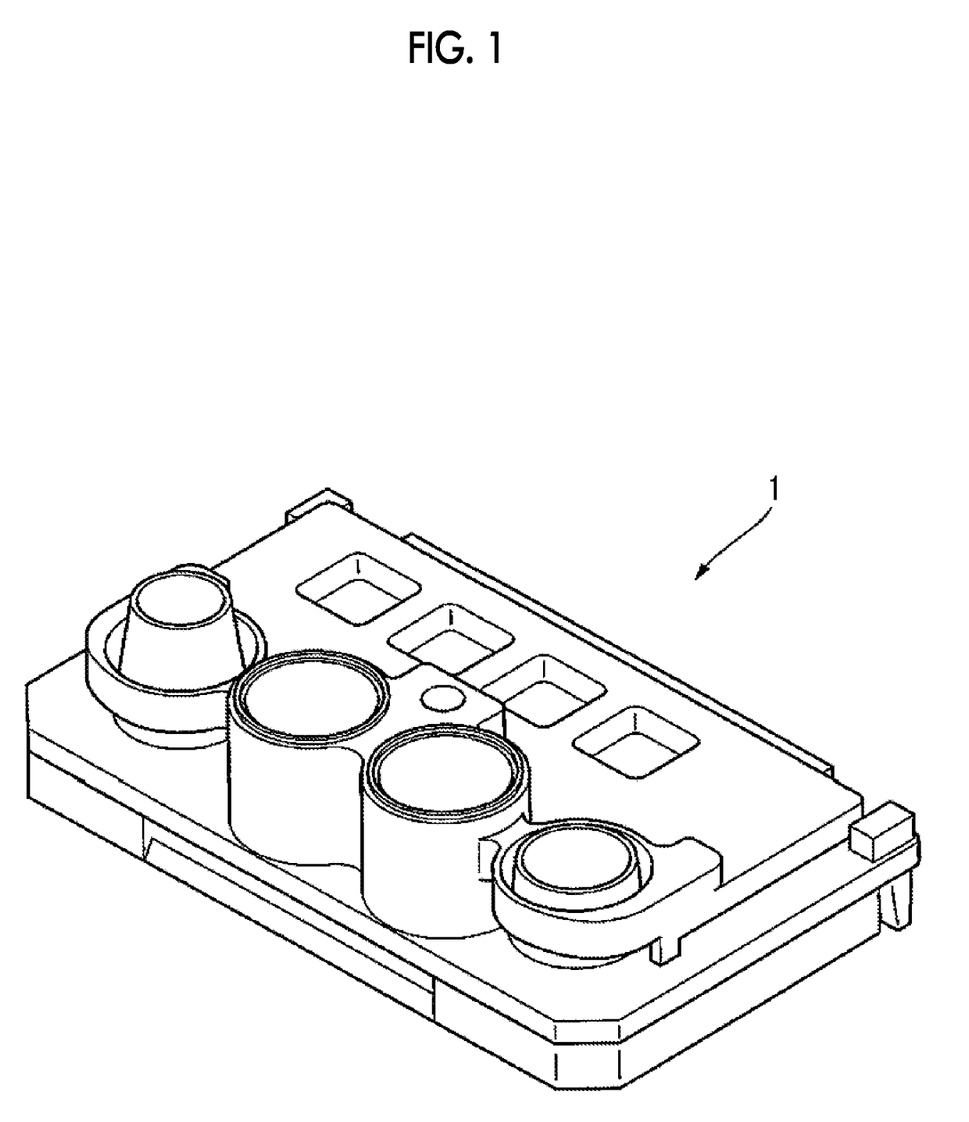
FIG. 1 shows a schematic view of a sensor chip provided in a kit of the present invention.
Figure 2:
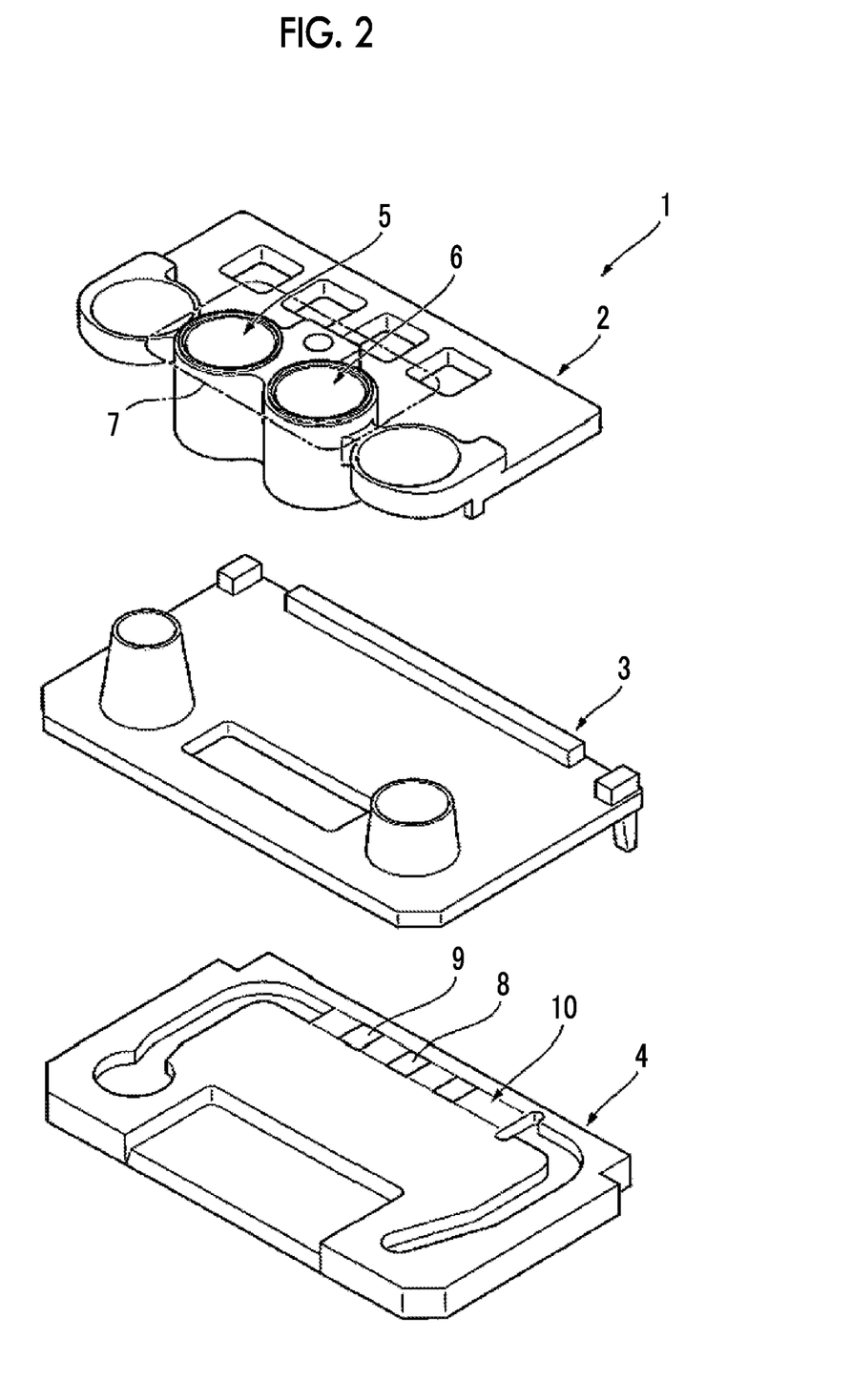
FIG. 2 shows an exploded view of the sensor chip provided in the kit of the present invention.

A flow passage-type sensor chip was produced so as to have the configuration of the second embodiment of JP2010-190880A. FIGS. 1 and 2 are schematic views of the sensor chip. FIG. 1 is the schematic view of a sensor chip 1, and FIG. 2 is an exploded view of the sensor chip 1. The sensor chip 1 is configured of an upper member 2, an intermediate member 3, and a substrate 4. The upper member 2 has a first container 5 and a second container 6. The first container 5 and the second container 6 are collectively referred to as a container group 7. A flow passage 10 is formed in the substrate 4, and a detection region 8 and a reference region 9 are formed on the flow passage 10.

(9) Measurement with Large Machine (Existing Bile Acid Measurement Reagent)

By immunoassay, samples having a known amount of bile acids were measured by using HITACHI 7170 AUTOMATIC ANALYZER, which is a large machine widely used by those skilled in the art, according to an instruction manual, and therefore measurement values of bile acids were obtained.

(10) Immunoassay of Bile Acids Using Fluorescent Particles

The samples having a known amount of bile acids which were measured in (9) was mixed in advance in a cup containing fluorescent particles 1 to which the three types of the bile acid antibodies prepared in (6-1) had been adsorbed, while stirring for 10 minutes. Next, the resultant was spotted on the each flow passage-type sensor chip in which the substrate 1 produced in (7) was installed. After spotting, the mixed solution was allowed to flow down at a rate of 10 μL/min while performing pump suction and brought into contact with the gold film surface to which the bile acid-BSA conjugate was immobilized, and then the intensity of fluorescence was continuously measured for 1.5 minutes. The increase rate of fluorescence intensity in unit time of each of the detection region and the reference region obtained in each substrate was obtained as a fluorescence signal value, and a signal value of the detection region was divided by a signal value of the reference region so as to carry out the standardization. In addition, a sample with a concentration of bile acids of 0 was prepared, and the fluorescence signal value was standardized in the same manner, and the signal value from the sample not containing bile acids was standardized.

(11) Creation of Calibration Curve

The fluorescence signal values standardized for the sample having the known amount of bile acids, which were obtained in (10), was allowed to correspond to the measurement value obtained by the large machine in (9), and therefore a calibration curve was created for the substrates prepared in (1-1) to (1-3) in which the bile acid-BSA conjugates-1 to 3 were used, respectively.

(12) Measurement Result of Sample Having Unknown Amount of Bile Acids

Serums 1 to 4 from dogs were obtained from Kitayama Labes Co., Ltd., experiments were carried out with a combination of fluorescent particles and a substrate as shown in Table 3, and therefore measurement values of bile acids were obtained by using the calibration curve created in (11). With respect to the above serums 1 to 4, the measurement values of bile acids were determined using the large machine.

Based on the measurement values of the large machine, a dissociation degree of the measurement values from the values of the present invention was calculated by the following calculation formula, and the results are summarized in Table 3.

Calculation Formula for Dissociation Width % from Large Machine $$\frac{|(\text{Measurement values of bile acids of large machine}) - (\text{measurement values of bile acids of the present invention})|}{(\text{Measurement values of bile acids of large machine})} \times 100$$

TABLE 3

| Serum | Fluorescent particle | Antibody | Substrate | Measurement values of large machine (μmol/L) | Measurement values of kit (μmol/L) | Dissociation width % from large machine | Note |
|---|---|---|---|---|---|---|---|
| 1 | 1 | Mixture of three types of antibodies | 1 | 50 | 50.3 | 0.6% | Example 1 |
| 1 | 2 | Cholic acid antibody | 1 | 65 | 40 | 38.4% | Comparative Example 1 |
| 1 | 3 | Deoxycholic acid antibody | 1 | 100 | 120 | 20% | Comparative Example 2 |
| 1 | 4 | Chenodeoxycholic acid antibody | 1 | 140 | 100 | 28.6% | Comparative Example 3 |
| 2 | 1 | Mixture of three types of antibodies | 1 | 20 | 20.1 | 0.5% | Example 2 |
| 3 | 1 | Mixture of three types of antibodies | 1 | 43 | 43 | 0.0% | Example 3 |
| 4 | 1 | Mixture of three types of antibodies | 1 | 85 | 85.2 | 0.2% | Example 4 |

Based on the results in Table 3, it was found that in the case where the fluorescent particles are fluorescent particles in which the three types of different antibodies are mixed and present, it is possible to accurately measure the bile acids which are the substances to be measured, and therefore the effect of the present invention was confirmed.

EXPLANATION OF REFERENCES

1: sensor chip
2: upper member
3: intermediate member
4: substrate
5: first container
6: second container
7: container group
8: detection region
9: reference region
10: flow passage

What is claimed is:

1. A kit for quantitatively determining a substance to be measured in a biological sample, the kit comprising:
   fluorescent particles that have a first binding substance capable of binding to the substance to be measured; and
   a substrate that has a detection region having a second binding substance capable of binding to any one of the substance to be measured and the first binding substance,
   wherein the substance to be measured includes at east three types of substances having different structures, and
   the first binding substance includes at least three types of binding substances which are capable of binding to the at least three types of substances having different structures, respectively, and
   each fluorescent particle of the fluorescent particles has the at least three types of binding substances, wherein the first binding substance includes a cholic acid antibody, a deoxycholic acid antibody, and a chenodeoxycholic acid antibody.

2. The kit according to claim 1,
wherein the second binding substance is the at least three types of substances having different structures or a conjugate of the three types of substances having different structures and a carrier.

3. The kit according to claim 1,
wherein the second binding substance includes a cholic acid and/or a cholic acid-albumin conjugate, a deoxycholic acid and/or a deoxycholic acid-albumin conjugate, and a chenodeoxycholic acid and/or a chenodeoxycholic acid-albumin conjugate.

4. The kit according to claim 1,
wherein the fluorescent particles are fluorescent latex particles.

5. The kit according to claim 1,
wherein the detection region is a gold film surface.

* * * * *